(12) United States Patent
Schweiger et al.

(10) Patent No.: US 6,420,288 B2
(45) Date of Patent: *Jul. 16, 2002

(54) PROCESS FOR THE PREPARATION OF SHAPED TRANSLUCENT LITHIUM DISILICATE GLASS CERAMIC PRODUCTS

(75) Inventors: Marcel Schweiger, Chur (CH); Sascha Cramer von Clausbruch, Rankwell (AT); Wolfram Höland, Schaan; Volker Rheinberger, Vaduz, both of (LI)

(73) Assignee: Ivoclar AG (LI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/187,716

(22) Filed: Nov. 6, 1998

Related U.S. Application Data

(60) Provisional application No. 60/072,164, filed on Jan. 22, 1998.

(30) Foreign Application Priority Data

Nov. 10, 1997 (DE) .......................... 197 50 794

(51) Int. Cl.⁷ .................. C03B 27/012; C03B 32/00
(52) U.S. Cl. .................. 501/7; 501/5; 501/64; 501/68; 501/69; 501/72; 106/35; 65/33.1; 65/33.4; 65/33.9; 65/102
(58) Field of Search .............. 106/35; 501/3, 501/7, 64, 68, 69, 72; 65/33.1, 33.4, 33.9, 102

(56) References Cited

U.S. PATENT DOCUMENTS

| | | | |
|---|---|---|---|
| 4,189,325 A | | 2/1980 | Barrett et al. |
| 4,515,634 A | | 5/1985 | Wu et al. |
| 5,507,981 A | * | 4/1996 | Petticrew .................. 264/16 |
| 5,698,482 A | * | 12/1997 | Frank et al. .................. 501/10 |
| 5,968,856 A | * | 10/1999 | Schweiger et al. ............ 501/7 |

FOREIGN PATENT DOCUMENTS

| | | |
|---|---|---|
| DE | 421886 | 12/1925 |
| EP | 0 231 773 A1 | 8/1987 |
| EP | 0 536 479 B1 | 9/1995 |
| EP | 0 536 572 B1 | 1/1996 |
| EP | 0 690 031 A1 | 1/1996 |
| EP | 0 827 941 A1 | 3/1998 |
| EP | 0 885 606 A2 | 12/1998 |
| FR | 655 264 A2 | 6/1991 |
| JP | 09-241345 | 9/1997 |
| JP | 10-165739 | 11/1998 |
| JP | 10-165741 | 11/1998 |

* cited by examiner

Primary Examiner—C. Melissa Koslow
(74) Attorney, Agent, or Firm—Nixon Peabody LLP

(57) ABSTRACT

A process is described for the preparation of shaped translucent lithium disilicate glass ceramic products which are characterized by high strength and good chemical stability and may be processed by pressing in the plastic state or milling to finished glass ceramic products which may be used in particular as dental restorations.

20 Claims, No Drawings

PROCESS FOR THE PREPARATION OF SHAPED TRANSLUCENT LITHIUM DISILICATE GLASS CERAMIC PRODUCTS

This application claims priority benefit of U.S. patent application Ser. No. 60/072,164, filed on Jan. 22, 1998, which is hereby incorporated by reference.

The invention relates to a process for the preparation of shaped translucent lithium disilicate glass ceramic products which can be prepared as blanks, which may be processed to shaped translucent dental products with high strength, particularly by plastic shaping with the action of pressure and heat or by machining.

Lithium disilicate glass ceramics are known from the prior art. Thus, self-glazed lithium disilicate glass ceramic articles are described in EP-B-536 479 but are not intended for dental purposes. The glass ceramics also contain no $La_2O_3$, and there is likewise no description of the preparation of blanks from the glass ceramic which, after processing, undergo a further heat treatment in order to complete crystallization. It is also necessary to carry out the heat treatment at a very low rate of heating of 5K/min in order to prevent stresses in the structure of the glass ceramic. Moreover, the glass ceramic is intended primarily for the preparation of tableware which naturally has only low translucence.

EP-B-536 572 also describes lithium disilicate glass ceramics which contain no $La_2O_3$. By scattering a finely divided coloured glass onto their surface, they receive structure and colour, and are used as lining elements for building purposes.

Lithium disilicate glass ceramics are disclosed in U.S. Pat. No. 4,189,325 which necessarily contain calcium oxide for improving the flow and also platinum and niobium oxide as special nucleating agents in order to produce very fine and uniform crystals. Even though the glass ceramic can be prepared in the form of blanks which have not yet crystallised completely, it is nevertheless free from $La_2O_3$.

WO-A-95/32678 and U.S. Pat. No. 5,507,981 describe lithium disilicate glass ceramics which may be processed to shaped dental products by hot pressing using a special pressable crucible. The glass ceramic materials are heated to such an extent, however, that crystals are no longer present in the molten material, otherwise the viscosity is too high for pressing to the dental product. Tests have shown that when the materials described are pressed by means of the process described in EP-A-231 773 and using the pressing furnace disclosed therein, an undesirably strong reaction occurs with the investment material used. Moreover, the glasses used show a very high rate of crystal growth, so that large crystals are produced during the heat treatment which impair the structure of the glass ceramic produced and consequently lead to products with poor strength.

Moreover, glass ceramics based on $SiO_2$ and $Li_2O$ are known from DE-C-1 421 886 which contain large quantities of arsenic trioxide which is physiologically very harmful.

A lithium disilicate glass ceramic which is suitable for the preparation of dental crowns and bridges but contains no $La_2O_3$ at all is disclosed in U.S. Pat. No. 4,515,634.

The glass ceramics described in FR-A-2 655 264 are free from $La_2O_3$. They contain lithium oxide and silicon oxide and very large quantities of MgO and are suitable for the preparation of dental prostheses.

Blanks of sintered ceramic based on leucite, feldspar or mica which are processed to dental products by computer-aided milling processes are also known from the prior art. These products have low strength, however, which is why said materials have not become established for highly stressed dental restorations.

The known lithium disilicate glass ceramics exhibit shortcomings when they are further processed to shaped products since an undesirably strong reaction with the investment material used during pressing occurs when they are processed in the plastic state using elevated temperatures and elevated pressures. Further processing of the glass ceramics by machining, such as milling, cannot usually be carried out satisfactorily due to the strength and toughness of the glass ceramics. Moreover, the conventional lithium disilicate glass ceramics frequently do not exhibit the high strengths and optical properties such as high translucence required for dental products and in many cases they also lack the chemical stability required for use as dental material which is permanently flushed with fluids of various kinds in the oral cavity.

The object of the invention is, therefore, to provide a process for the preparation of shaped translucent lithium disilicate glass ceramic products which have good chemical stability, a low density of defects, and high translucence with simultaneously good mechanical properties and exhibit only little reaction with the investment material used when further processed by pressing in the plastic state, and the glass ceramic products may also be prepared in the form of blanks with a low degree of crystallisation which may be shaped easily in the desired manner by mechanical means such as machining and may be converted to a high-strength glass ceramic product by a subsequent heat treatment.

Said object is achieved by the process for the preparation of shaped translucent lithium disilicate glass ceramic products.

The invention also relates to the shaped glass ceramic products, the use of such products and the shaped dental products.

The process according to the invention for the preparation of shaped translucent lithium disilicate glass ceramic products is characterised in that (a) a melt of a starting glass is produced which contains the following components:

| Component | Wt. % |
| --- | --- |
| $SiO_2$ | 57.0 to 80.0 |
| $Al_2O_3$ | 0 to 5.0 |
| $La_2O_3$ | 0.1 to 6.0 |
| MgO | 0 to 5.0 |
| ZnO | 0 to 8.0 |
| $Li_2O$ | 11.0 to 19.0 | where
(i) $Al_2O_3$ + $La_2O_3$ accounts for 0.1 to 7.0 wt. % and
(ii) MgO + ZnO accounts for 0.1 to 9.0 wt. %, (b) the melt of the starting glass is shaped in the desired manner and cooled, and (c) the shaped glass product is subjected to at least one heat treatment in the temperature range from 400 to 1100° C. in order to obtain a shaped glass ceramic product in the form of a blank.

In process stage (a), a melt of a starting glass is produced, to which end suitable starting materials, such as carbonates, oxides, phosphates and fluorides, are intimately mixed and heated to temperatures of, in particular, 1200 to 1600° C. In order to obtain a particularly high degree of homogeneity, the glass melt obtained may be poured into water to form glass granules and the glass granules obtained are melted again at temperatures of, in particular, 1200 to 1600° C. for 1 to 4 hours.

The melt of the starting glass preferably contains at least one of the following further components:

| Component | Wt. % |
|---|---|
| $ZrO_2$ | 0 to 10.0 |
| $K_2O$ | 0 to 13.5 |
| $P_2O_5$ | 0 to 11.0 |
| Colour and fluorescent components | 0 to 8.0 |
| Additional components | 0 to 6.0 |

Surprisingly, it was established that the additional incorporation of $ZrO_2$ led to an increase in translucence, although the opposite effect was observed in the conventional glass ceramic according to EP-B-536 479.

Ranges that may be chosen independently of one another, unless otherwise specified, exist for the quantities of the individual components, said ranges being as follows:

| Component | Wt. % |
|---|---|
| $SiO_2$ | 57.0 to 75.0 |
| $Al_2O_3$ | 0 to 2.5 |
| $La_2O_3$ | 0.1 to 4.0 |
| MgO | 0.1 to 5.0 |
| ZnO | 0 to 6.0, particularly 0.1 to 5.0 |
| $ZrO_2$ | 0 to 8.0, particularly 0.1 to 8.0 |
| $K_2O$ | 0 to 9.0, particularly 0.5 to 7.0 |
| $Li_2O$ | 13.0 to 19.0 |
| $P_2O_5$ | 0 to 8.0, particularly 0.5 to 8.0 |
| colour and fluorescent components | 0.1 to 8.0 |
| additional components | 0 to 3.0. |

For example oxides of f-elements may be used as colour components or fluorescent components. In preference, at least one of the following compounds is used.

| Component | Wt. % |
|---|---|
| $CeO_2$ | 0.1 to 5.0 |
| $V_2O_5$ | 0.01 to 1.0 |
| $Fe_2O_3$ | 0.01 to 1.0 |
| $MnO_2$ | 0.01 to 3.0 |
| $TiO_2$ | 0.01 to 5.0 |
| $Y_2O_3$ | 0.01 to 2.0 |
| $Er_2O_3$ | 0.001 to 2.0 |
| $Tb_2O_3$ | 0.001 to 2.0 |
| $Eu_2O_3$ | 0.001 to 2.0 |
| $Yb_2O_3$ | 0.001 to 2.0 |
| $Gd_2O_3$ | 0.001 to 2.0 |
| $Nd_2O_3$ | 0.001 to 2.0 |
| $Pr_2O_3$ | 0.001 to 2.0 |
| $Dy_2O_3$ | 0.001 to 2.0 |
| $Ag_2O$ | 0.01 to 2.0 |
| $SnO_2$ | 0.01 to 3.0 |
| $Ta_2O_5$ | 0.001 to 2.0 |

The special oxides that can be used as colour or fluorescent components in the process according to the invention ensure that the colour of the glass ceramic product can be matched easily to the application in question. This is particularly important if the glass ceramic products are to be used as dental products, the colour of which must be matched specially to that of the natural tooth material of the patient in question. The colour spectrum that can be obtained with these special oxides ranges from very pale shades to deep grey-brown shades e.g. in the case of non-vital tooth stumps. The fluorescence of the natural tooth material is imitated by any fluorescent components present. A particular advantage of the colour and fluorescent components used according to the invention is that they do not interfere with the structure of the glass ceramic products produced in such a manner that non-homogeneous materials with a high density of defects and high porosity are produced. This problem frequently occurs with sintered ceramics, the colour of which is altered by the addition of pigments. In order to prevent any deterioration in their colouring effect, said pigments are not usually added until prior to the sintering process carried out at relatively low temperatures so that they are always present as crystals or crystallites which lead to non-homogeneities.

Apart from the components mentioned above, the starting glass may also contain additional components for which in particular $B_2O_3$, $Na_2O$, BaO, F and/or SrO are suitable.

Preferably, the melt of the starting glass is composed of the components mentioned in the stated quantities.

Moreover, the melt of the starting glass is shaped in the desired way in stage (b) and cooled. Shaping takes place in particular by pouring the melt into a desired mould. It is also possible for compaction of the melt by pressure to take place after pouring in order to achieve a particularly good homogeneity and accurate reproduction. It is possible to proceed in such a manner that a glass droplet is introduced into the desired mould and then compacted by pressing.

The melt is cooled particularly in a controlled manner so as to prevent stresses in the structure associated with rapid temperature changes and to prevent cracks and fissures that may possibly result from said stresses. As a rule, the melt is therefore poured into preheated moulds or cooled slowly in a furnace.

Finally, the shaped glass product formed undergoes at least one heat treatment in stage (c) in order to bring about the crystallisation thereof. When this process stage has ended, a shaped glass ceramic product in the form of a blank is obtained. This blank usually takes the form of a small cylinder or a rectangular block. The heat treatment takes place preferably at a temperature of less than 1000 and particularly less than 900° C. The shaped glass product is preferably introduced into a furnace already heated to the temperature mentioned. In contrast to conventional materials, it is not necessary to select a slow rate of heating in order to prevent stresses. The special composition and method of preparation of the material according to the invention is apparently responsible for this advantageous behaviour.

The degree of crystallisation and the crystal size in this glass ceramic blank may be varied very widely by the type of heat treatment selected. On the one hand it is possible to produce a glass with only nuclei or very small crystals in the sub-micron region, which thus represents the simplest form of a glass ceramic, or on the other hand to form a fully crystallised glass ceramic. In each case, the ceramic production process takes place by way of the mechanism of volume crystallisation, and volume nucleating agents such as e.g. $P_2O_5$ present in the starting glass used play an important part in the formation of finely divided crystals in the structure.

In particular the following two possibilities (d1) and (d2) are available for producing the final glass ceramic product, such as a dental bridge or a dental crown.

On the one hand, the glass ceramic product in the form of a blank may undergo plastic shaping in stage (d1) to a glass ceramic product of the desired geometry at a temperature of 700 to 1200° C. and by the application of pressure, particularly of 8 to 40 bar. It is preferable for this forming stage to use the process described in EP-A-231 773 for the production of dental restorations and to use the pressing furnace likewise disclosed therein. In said process, the blank is pressed in the plastic state into a mould cavity corresponding to the desired shaped dental product, such as crowns, using heat and pressure. The pressing furnace used in particular for this purpose is sold as the Empress ® furnace by Ivoclar AG, Liechtenstein.

It has become apparent that conventional lithium disilicate glass ceramics exhibit an unacceptably strong reaction with the investment material used during further processing to glass ceramic products, have insufficient flow properties or exhibit uncontrolled crystal growth. These disadvantages are avoided in the process according to the invention by the use of $La_2O_3$ and optionally $Al_2O_3$ in the stated quantities in the starting glass. As a result, the glass ceramic product in the form of a blank may be processed in an advantageous manner by pressing in the plastic state to a glass ceramic product of the desired geometry, particularly a dental product such as a dental restoration.

It is also possible to process the glass ceramic product in the form of a blank by machining in stage (d2), particularly by CAD/CAM-based milling devices, to obtain a glass ceramic product of the desired geometry. A so-called chairside treatment is thus possible for the dentist. When this variant of further processing is carried out, the glass ceramic blank used in particular is one which is not yet fully crystallised but is present e.g. only as a nucleus-containing glass blank or glass ceramic blank with very small crystals. Such glass ceramic blanks that have not yet fully crystallised have the particular advantage that they may be machined to the finished glass ceramic product of the desired geometry in a markedly easier manner than conventional glass ceramics. In order to produce a glass ceramic blank in which the glass matrix contains only nuclei or very small crystallites, it has proved to be particularly advantageous to carry out the heat treatment performed in stage (c) at a temperature of 400 to 900° C. In each case, the degree of crystallinity of the glass ceramic blank used may be adapted to the type of machining desired so that said machining may be carried out as easily as possible.

After the subsequent machining in stage (d2), the shaped glass ceramic product obtained then undergoes at least one further heat treatment, particularly at 700 to 900° C., in order to achieve further crystallisation and hence solidification of the glass ceramic product. The fracture strength, colour and translucence are improved by this further heat treatment.

The finished glass ceramic product of the desired geometry present after further processing, particularly in stages (d1) and (d2), may ultimately be provided with a coating, which is advantageous if it is used in the dental field. Suitable coatings are in particular a ceramic, a sintered ceramic, a glass ceramic, preferably an apatite glass ceramic, a glass, a glaze and/or a composite. Those coatings that have a sintering temperature of 650 to 950° C. and a linear thermal expansion coefficient that is smaller than that of the glass ceramic product to be coated are advantageous. Coatings whose thermal expansion coefficient deviates by not more than $\pm 3.0 \times 10^{-6}$ $K^{-1}$ from that of the substrate are particularly suitable.

A coating is applied in particular by sintering on. During this sintering process, the glass ceramic product containing the lithium disilicate glass ceramic is, however, brought to a temperature range which lies above the transformation point of the residual glass matrix of the glass ceramic. In so doing, conventional lithium disilicate glass ceramics are frequently deformed in an unwanted manner because their dimensional stability on heating is too low. The glass ceramic product prepared according to the invention, however, shows excellent dimensional stability on heating, for which in particular the $La_2O_3$ content and possibly the $Al_2O_3$ content in the stated quantities is responsible.

The glass ceramic products prepared according to the invention are particularly suitable for use as dental products or constituents thereof due to their properties. Preferred glass ceramic products have a 3-point bending strength of more than 400 MPa if they are prepared according to process variant (d1) and of more than 250 MPa if they are prepared according to process variant (d2). The process used to determine the 3-point bending strength is explained in the Examples.

Moreover, the glass ceramic products according to the invention have a translucence comparable with that of the natural tooth. In order to quantify the translucence, the CR value was determined according to the method described in the Examples. The CR value, also known as the contrast ratio, indicates the ratio of light reflection of a specimen of the glass ceramic on a black background to the measurement of light reflection of a specimen on a white background and thus serves as a measure of the translucence of a material. The CR value is defined by the following formula:

$$CR = Y_b / Y_w$$

where
CR=contrast ratio
$Y_b$=light reflection of the specimen on a black background, and
$Y_w$=light reflection of the specimen on a white background.

The CR value is always between 0 and 1, whith CR=0 standing for an opacity of 0% and consequently a completely translucent material, and CR=1 standing for an opacity of 100% and consequently a completely opaque material, i.e. one which is impervious to light.

The glass ceramic product according to the invention usually has a CR value of 0.05 to 0.9 and preferably 0.1 to 0.75, in each case measured with a sample thickness of 1.2 mm.

Analyses of the glass ceramic product according to the invention have also shown that this has a very homogeneous structure with uniformly distributed fine crystals. It is assumed that this special structure is brought about by the particular composition of the starting glass used and by the shaping, particularly pouring solid glass blanks in stage (b), and is responsible for the particularly high strength of the glass ceramic product eventually obtained.

It is also surprising that the colour, translucence and fluorescence of the glass ceramic product according to the invention may be matched to that of a natural tooth without the colour and fluorescent components used adversely affecting the strength and toughness of the glass ceramic. In contrast, it is known that with glass ceramics based on leucite, crystallisation is considerably affected by such additives and the strength is often very much reduced. It is known that the pigments used in many cases in sintered ceramics lead to a very high density of defects and to pore formation in the glass ceramic, which in turn impairs the properties thereof.

Finally, the glass ceramic product according to the invention is characterised by excellent acid resistance, which is preferably less than 100 $\mu g/cm^2$ loss of mass. Said loss of mass was determined by the method explained in the Examples in which the glass ceramic is treated with aqueous acetic acid over a certain period and the loss of mass ascertained after the treatment serves as a measure of acid resistance.

Preferred shaped dental products which contain the glass ceramic product according to the invention are dental restorations such as an inlay, an onlay, a bridge, an abutment, a facing, a veneer, a facet, a crown or a partial crown.

Moreover, preferred shaped dental products are those in the form of blanks or ingots, i.e. which undergo further processing to the final dental product, e.g. according to stages (d1) and (d2). Such blanks may be present in various forms adapted to the further processing method in question, such as small cylinders or rectangular blocks.

The invention is explained in more detail below on the basis of Examples.

EXAMPLES

Examples 1 to 20

A total of 20 different glass ceramic products according to the invention with the chemical compositions given in Table I were prepared by carrying out stages (a) to (c) of the process described.

crucible at a temperature of 1500° C. and for a homogenisation time of 2 hours. The glass melt obtained was granulated by pouring into water and the glass frit formed was dried. The glass frit was then milled again in a ball mill and melted again at 1500° C. for a homogenisation time of 2 hours. The homogeneous, transparent and slightly yellow coloured melt obtained was then poured into a steel mould preheated to 500° C. to form cylindrical rods which were cooled slowly in a controlled manner in a furnace from 500° C. to room temperature. The glass rods obtained were sawn into specimens of 2 g, 3 g and 4 g and then heat-treated for 30 minutes at 870° C. in order to form the corresponding glass ceramic blanks. The cooled glass rods were placed directly in the furnace preheated to 870° C. A slow rate of heating was not required.

Properties of the Blanks

The glass ceramic blanks obtained had optical properties such as e.g. translucence, colour and cloudiness comparable with those of commercial dental ceramic products, e.g. IPS Empress blanks from Ivoclar AG, Liechtenstein.

A. 3-point Bending Strength

In order to determine the 3-point bending strength, rods were prepared as specimens from the glass ceramic blanks

TABLE I (amounts in wt. %)

| Example | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| $SiO_2$ | 67.9 | 66.6 | 69.42 | 68.86 | 68.5 | 68.1 | 64.9 | 68.1 | 67.6 | 74.95 | 61 | 71.7 | 67.6 | 66.5 | 67.9 | 61.3 | 63.7 | 65.6 | 66.7 | 65.8 |
| $K_2O$ | 4.2 | 4.1 | 4.3 | 4.3 | 4.2 | 4.2 | 5.2 | 4.2 | 4.1 | 2 | 7.8 | 4.4 | 4.1 | 3.5 | 4.2 | 13.5 | 4 | 4.1 | 4.1 | 4.1 |
| $Li_2O$ | 15 | 14.7 | 15.4 | 15.3 | 15.1 | 15.1 | 16.1 | 15 | 15 | 17 | 11 | 15.9 | 14.9 | 15.6 | 15.1 | 13.8 | 14 | 14.5 | 14.8 | 14.6 |
| $Al_2O_3$ | 1.1 | 1 | 1.1 | 1.1 | 1.1 | 1.1 | 1.1 | 1.1 | 1.1 | 0.5 | 2 | | 1.1 | 1.5 | 1.1 | 1 | 1 | 1.1 | 1.1 | 1.1 |
| $P_2O_5$ | 3.8 | 3.7 | 3.8 | 3.8 | 3.8 | 3.8 | 3.7 | 3.8 | 3.8 | 1.8 | 7 | | 3.8 | 2.5 | 3.7 | 3.4 | 3.6 | 3.7 | 3.7 | 3.7 |
| MgO | 0.1 | 0.1 | 0.1 | 0.1 | 0.1 | 0.1 | 0.1 | 0.1 | 0.1 | 0.05 | 0.2 | 0.1 | 0.1 | 0.1 | 0.1 | 0.1 | 0.1 | 0.1 | 0.1 | 0.1 |
| $TiO_2$ | 1.6 | 1.6 | | 0.3 | | | | | | | | | | 0.2 | | | | 0.2 | | |
| $ZrO_2$ | | 2 | | | | | | | | | | | | | | | 6.1 | 4 | | 3 |
| ZnO | 4.8 | 4.7 | 4.9 | 4.9 | 4.8 | 4.8 | 5.8 | 4.8 | 4.8 | 2.3 | 8 | 5.1 | 4.8 | 5 | 4.8 | 4.1 | 4.6 | 4.7 | 4.7 | 4.7 |
| $CeO_2$ | 0.5 | 0.5 | 0.6 | 0.6 | 2 | 2 | 2 | 2 | 2 | 1 | 2 | 2 | 2 | 2 | 2 | 2 | 2 | 0.5 | 2 | |
| $MnO_2$ | 0.53 | 0.53 | | 0.32 | | | | | | | | | | 1.8 | | | | | | |
| $Fe_2O_3$ | 0.17 | 0.17 | | 0.12 | | | | | | | | | | | | | | | | |
| $La_2O_3$ | 0.3 | 0.3 | 0.3 | 0.3 | 0.3 | 0.3 | 0.3 | 0.3 | 0.3 | 0.15 | 0.5 | 0.3 | 0.3 | 0.3 | 0.3 | 0.3 | 0.3 | 1 | 0.3 | 2 |
| $Ag_2O$ | | | 0.08 | | | | | | | | | | | | | | | | | |
| $V_2O_5$ | | | | | 0.1 | 0.1 | 0.2 | 0.6 | 0.6 | 0.1 | 0.2 | 0.2 | | 0.1 | 0.2 | 0.2 | 0.2 | | 0.2 | |
| $Er_2O_3$ | | | | | | 0.1 | 0.3 | | | | | | | 0.1 | | | | | | |
| $Tb_4O_7$ | | | | | | | 0.3 | | 0.4 | | | | | 1.1 | | | | | | |
| $Eu_2O_3$ | | | | | | | | 0.3 | | | | | | | | | | | | |
| $Pr_2O_3$ | | | | | | | | | | 0.15 | 0.3 | 0.3 | | | 0.3 | 0.6 | 0.3 | 0.6 | 0.3 | |
| $Y_2O_3$ | | | | | | | | | 0.2 | | | | | | 0.5 | | | | | 0.6 |
| $Dy_2O_3$ | | | | | | | | | | | | | | | | | | 0.5 | | |
| $SnO_2$ | | | | | | | | | | | | | | | | | | | 2 | |
| $Ta_2O_5$ | | | | | | | | | | | | | | | | | | | | 0.3 |

Example 21

Dental Product Prepared by Hot Pressing According to EP-A-231 773

This Example describes the preparation of a glass ceramic blank according to the invention which may be used for the preparation of an individually shapable all-ceramic dental product, such as a crown or a multi-span bridge. In addition, a matched dental sintered ceramic may then be sintered onto the dental product.

Initially, a starting glass with the chemical composition given in Table I for Example 14 was prepared. To this end, a batch of appropriate oxides, carbonates and phosphates was mixed in a ball mill and melted in a platinum-rhodium according to ISO dental standard 6872/1995. The 3-point bending strength was then determined likewise according to ISO 6872-1995 E "Dental Ceramic" with a rate of advance of load application of 0.5 mm/min and a distance of 15 mm between the supports of the specimen. The bending strength determined under these conditions was 408±63 MPa.

Properties of Glass Ceramic Having Undergone Plastic Shaping

The glass ceramic blanks obtained were pressed using the hot pressing process according to EP-A-231 773 and the pressing furnace likewise described therein in vacuo in the viscous state, to obtain the desired specimen geometry for the test in question. The standby temperature of the pressing furnace was 800° C., the rate of heating to the pressing temperature was 60° C./min, the pressing temperature was 910° C., the holding time at the pressing temperature was 15 minutes and the pressing pressure reading was 5 bar. After the pressing process, the pressing mould was cooled in the air and the shaped glass ceramic products obtained were removed from the mould by sand blasting with $Al_2O_3$ powder and glass beads. The products had the following properties.

A. Optical Properties

In order to quantify the translucence of the glass ceramic products, the CR value was determined according to the method of measurement of the British Standards Institution which is described in the dental ceramic test standard "BS 5612: 1978".

To this end, 5 specimens with a diameter of 16 mm and a sample thickness of 1.4 mm were prepared. The specimens were ground with wet SiC powder, grain 320, in order to obtain the desired surface wet SiC powder, grain 320, in order to obtain the desired surface quality (surface roughness Ra=0.8 µm to 1.6 µm). It is important that the plane-parallelism of the opposite sides does not exceed a tolerance of ±0.01 mm since the measuring result depends to a large extent on the film thickness. The final sample height/thickness was 1.2±0.025 mm.

The specimens were placed in the provided opening of a Minolta-CR300 colour measuring instrument and the reflection of each of the 5 specimens was measured with an aperture of 10 mm. The samples must not be in optical contact with the background during the measurement, a situation which may be prevented, if necessary, by applying a drop of glycerine onto the background.

(a) In order to determine the sample emission on a black background $Y_b(Y_{black})$ a black plate with not more than 4% reflection was used.
(b) In order to determine the sample emission on a white background $Y_w(Y_{white})$, a white plate with a reflection of 80% to 85% was used.

The contrast value $CR=Y_b/Y_w$ was then determined from the values $Y_b$ and $Y_w$ determined, and this was 0.63.

As a result of the translucent properties, this glass ceramic product was suitable as an all-ceramic dental product which conforms optically with the specifications of a natural tooth. Due to the use of glass-colouring oxides in the starting glass, the hot-pressed glass ceramic product was tooth-coloured, and it was possible to adjust the intensity and shade of the colour by means of the concentration of the colourant oxides.

A translucent to transparent dental sintered glass ceramic with an expansion coefficient of $9.5 \times 10^{-6}$ $K^{-1}$ (100 to 400° C.) could be applied as a coating to the translucent glass ceramic product employable as a framework material. The dental sintered glass ceramic was sintered in layers onto the glass ceramic product in vacuo at 760° C., which led to translucent all-ceramic dental restorations which meet the stringent aesthetic requirements of such products.

B. 3-point Bending Strength

The 3-point bending strength was determined on hot-pressed glass ceramic rods in accordance with the method used above for the blanks. A 3-point bending strength of 450±85 MPa was determined.

C. Thermal Expansion Coefficient

To this end, cylindrical glass ceramic samples with a diameter of 6 mm and a length of 20 mm were hot-pressed. The expansion coefficient determined for these samples in the temperature range of 100 to 500° C. was $10.8 \times 10^{-6}$ $K^{-1}$.

D. Fracture Touchness $K_{IC}$

To this end, glass ceramic rods with the dimensions 20×4.4×1.4 $mm^3$ were hot-pressed and then reground on all sides with SiC wet-grinding paper (1000 grain). Using a diamond cutting wheel (0.2 mm thick), the samples were notched on one side as far as the centre to a depth of 2.2 mm and then tested according to DIN 51 109 with an outer distance between the supports of 15 mm and a rate of advance of load application of 0.5 mm/min using the 4-point bending test arrangement. The $K_{IC}$ value determined was 3.0±0.3 MPa √ m.

E. Acid Resistance

To this end, disc-shaped glass ceramic samples with a diameter of 15 mm and a thickness of 1.5 mm were hot-pressed and then reground on all sides with SiC wet-grinding paper (1000 grain). according to ISO 6872-1995 E "Dental Ceramic" was determined after 16 hours' storage in 4 vol. % aqueous acetic acid solution. The value was 36 µg/$cm^2$ and was markedly below the standard value for dental ceramics of 2000 µg/$cm^2$.

Example 22

Dental Product Prepared by Computer-aided Milling Technology

This Example describes the preparation of a glass ceramic blank according to the invention which is processed by machining and subsequently by a further heat treatment to an individually shaped all-ceramic dental product, such as a crown or a multi-span bridge, onto which a matched translucent to transparent dental sintered ceramic may be sintered on in addition.

The dental product was produced by means of a CAD/CAM method, such as CEREC 2®, from Siemens AG.

Only the heat treatment carried out after machining resulted in the dental product with the good mechanical characteristics such as 3-point bending strength and the good optical properties required for a dental ceramic product.

A starting glass with the composition given in Table I for Example 7 was prepared initially. To this end, a batch of oxides, carbonates and phosphates was mixed in a ball mill and melted in a platinum/rhodium crucible at a temperature of 1500° C. and for a homogenisation time of 2 hours. The glass melt was fritted by pouring into water and the frit was milled after drying in a ball mill and melted again at 1500° C. for a homogenisation time of 2 hours. The homogeneous, transparent and slightly yellow coloured melt obtained was then poured into a steel mould preheated to 500° C. to obtain rectangular blocks with the dimensions 65×20×16 $mm^3$ and cooled slowly in a controlled manner from 500° C. to room temperature in a furnace. The rectangular glass blocks obtained were sawn into samples with the dimensions 18×14×20 obtained were sawn into samples with the dimensions 18×14×20 $mm^3$. These samples were then heat-treated for 60 minutes at 650° C. The cooled glass blocks were introduced directly into the furnace heated to 650° C. The glass ceramic blanks obtained after this first heat treatment stage had the following properties.

Properties of the Blanks After a Single Heat Treatment (650° C./1 h)

A. Optical Properties

The glass ceramic blanks had a violet-whitish colour. They had a CR value of 0.36 determined according to the method described in Example 21.

B. 3-point Bending Strength

The 3-point bending strength determined according to Example 21 for the glass ceramic blanks was 171±20 MPa.

Preparation and Properties of the Finished Glass Ceramic

The glass ceramic blanks which had undergone a single heat treatment were processed to dental ceramic restorations such as, e.g., crowns using a computer-aided milling machine. In view of the relatively low strength and toughness of the glass ceramic blanks, processing proved to be easy to carry out. Compared with known milling ceramics, they brought about less tool wear and fewer breakages were formed, this being attributable to the finer structure and absence of defects.

The milled dental restoration then underwent a further heat treatment at 760° C. for 1 h. This temperature was selected because there is no risk of deformation of the framework at said temperature. This additional heat treatment led to a more thorough crystallisation and hence a change in the properties of the restoration. The glass ceramic obtained which had undergone two treatments had the following properties.

A. Optical Properties

The glass ceramic was translucent and tooth-coloured due to the use of glass-colouring oxides in the starting glass.

The CR value determined for this glass ceramic according to Example 21 using cylindrical samples with a diameter of 16 mm and thickness of 1.2 mm was 0.23.

B. 3-point Bending Strength

The 3-point bending strength of the glass ceramic determined according to Example 21 was 272±24 MPa.

C. Linear Thermal Expansion Coefficient

To this end, rectangular specimens with the dimensions 30×4×3 mm$^3$ were sawn out of solid blocks that had undergone two heat treatments. The expansion coefficient determined for these samples in the temperature range from 100 to 500° C. was $10.9 \times 10^{-6} K^{-1}$.

D. Fracture Toughness $K_{IC}$

The fracture toughness determined according to Example 21 on rods from solid blocks that had undergone two heat treatments was 2.1±0.1 MPa √m.

E. Acid Resistance

The acid resistance determined according to Example 21 on samples of glass ceramic which had undergone two heat treatments was 16 μg/cm$^2$ and was thus markedly below the standard value for dental ceramic materials of 2000 μg/cm$^2$ and lower than that of conventional dental framework materials.

Finally a translucent to transparent sintered glass ceramic with an expansion coefficient of $9.5 \cdot 10^{-6} \times K^{-1}$ was sintered in layers in vacuo at 760° C. and with a holding time of 2 minutes in each case, onto the milled, twice heat-treated glass ceramic. A finished dental restoration was thereby obtained.

Examples 23 to 26

In these Examples, hot-pressed glass ceramic products were prepared according to Example 21 and their properties were tested. The starting glasses used, however, were glasses with the composition given in Table I for Examples 1, 4, 18 and 20.

The properties determined for these glass ceramics and the glass ceramics according to Example 21 and 22 are listed in Table II.

TABLE II

| Examples (starting glass) | Process | Bending strength [MPa] | Fracture toughness [MPa*√m] | Thermal expansion coefficient (100° C.–500° C.) [μm/mK] | Acid resistance [μg/cm$^2$] | Fluorescence (at a wavelength of 366 nm) | Translucence CR value (sample thickness 1.2 mm) | Colour |
|---|---|---|---|---|---|---|---|---|
| Example 21 (glass no. 14) | d1 | 450 ± 85 | 3.0 ± 0.3 | 10.8 | 36 | white-yellow | 0.63 | white-beige |
| Example 22 (glass no. 7) | d2 | 272 ± 24 | 2.1 ± 0.1 | 10.9 | 16 | orange | 0.23 | grey-beige |
| Example 23 (glass no. 1) | d1 | 386 ± 71 | | 10.7 | 22 | | | white-beige |
| Example 24 (glass no. 4) | d1 | 453 ± 93 | | 10.5 | 34 | | | white-yellow |
| Example 25 (glass no. 18) | d1 | 336 ± 63 | | | | white-yellow | 0.41 | yellowish-transparent |
| Example 26 (glass no. 2) | d1 | 343 ± 15 | | | | dark violet | 0.37 | whitish-transparent |

What is claim is:

1. A process for the preparation of shaped translucent lithium disilicate glass ceramic products, which comprises
   (a) producing a melt of a starting glass containing the following components

| Component | Wt. % |
|---|---|
| SiO$_2$ | 57.0 to 80.0 |
| Al$_2$O$_3$ | 0 to 5.0 |
| La$_2$O$_3$ | 0.1 to 6.0 |
| MgO | 0 to 5.0 |
| ZnO | 0 to 8.0 |
| Li$_2$O | 11.0 to 19.0 | where
(i) Al$_2$O$_3$ + La$_2$O$_3$ accounts for 0.1 to 7.0 wt. % and
(ii) MgO + ZnO accounts for 0.1 o 9.0 wt. %, (b) shaping the melt of the starting glass and cooling it, and
   (c) subjecting the shaped glass product to at least one heat treatment in the temperature range from 400 to 1100° C. in order to obtain a shaped glass ceramic product in the form of a blank.

2. A process according to claim 1, wherein
   (d1) the glass ceramic product in the form of a blank is subjected to plastic shaping at a temperature of 700 to 1200° C. and by the application of pressure to obtain a glass ceramic product of the desired geometry.

3. A process for the preparation of shaped translucent lithium disilicate glass ceramic products, which comprises
   (a) producing a melt of a starting glass containing the following components

| Component | Wt. % |
| --- | --- |
| $SiO_2$ | 57.0 to 80.0 |
| $Al_2O_3$ | 0 to 5.0 |
| $La_2O_3$ | 0.1 to 6.0 |
| ZnO | 0 to 8.0 |
| $Li_2O$ | 11.0 to 19.0 | where
(i) $Al_2O_3 + La_2O_3$ accounts for 0.1 to 7.0 wt. % and
(ii) $MgO + ZnO$ accounts for 0.1 to 9.0 wt. %, (b) shaping the melt of the starting glass and cooling it, (c) subjecting the shaped glass product to at least one heat treatment in the temperature range from 400 to 1100° C. in order to obtain a shaped glass ceramic product in the form of a blank, and (d2) processing the glass ceramic product in the form of a blank by machining to a glass ceramic product of the desired geometry.

4. A process according to claim 3, wherein a blank is used in (d2) which has undergone a heat treatment at 400 to 900° C. during step (c).

5. A process according to claim 3, wherein the shaped glass ceramic product of the desired geometry obtained in stage (d2) is subjected to at least one further heat treatment.

6. A process according to claim 1, wherein the heat treatment in stage (c) is carried out at a temperature of less than 1000° C.

7. A process according to claim 1, wherein the shaped glass ceramic product of the desired geometry is provided with a coating.

8. A process according to claim 7, wherein the coating is a ceramic, a sintered ceramic, a glass ceramic, a glass, a glaze and/or a composite.

9. A process according to claim 1, wherein the melt of the starting glass contains at least one of the following further components:

| Component | Wt. % |
| --- | --- |
| $ZrO_2$ | 0 to 10.0 |
| $K_2O$ | 0 to 13.5 |
| $P_2O_5$ | 0 to 11.0 |
| Colour and fluorescent components | 0 to 8.0 |
| Additional components | 0 to 6.0. |

10. A process according to claim 9, wherein the quantities of components are selected independently of one another as follows:

| Component | Wt. % |
| --- | --- |
| $SiO_2$ | 57.0 to 75.0 |
| $Al_2O_3$ | 0 to 2.5 |
| $La_2O_3$ | 0.1 to 4.0 |
| MgO | 0.1 to 5.0 |
| ZnO | 0 to 6.0 |
| $ZrO_2$ | 0 to 8.0 |
| $K_2O$ | 0 to 9.0 |
| $Li_2O$ | 13.0 to 19.0 |
| $P_2O_5$ | 0 to 8.0 |
| colour and fluorescent components | 0.1 to 8.0 |
| additional components | 0 to 3.0. |

11. A process according to claim 9, wherein the colour or fluorescent component used is at least one of the following compounds:

| Component | Wt. % |
| --- | --- |
| $CeO_2$ | 0.1 to 5.0 |
| $V_2O_5$ | 0.01 to 1.0 |
| $Fe_2O_3$ | 0.01 to 1.0 |
| $MnO_2$ | 0.01 to 3.0 |
| $TiO_2$ | 0.01 to 5.0 |
| $Y_2O_3$ | 0.01 to 2.0 |
| $Er_2O_3$ | 0.001 to 2.0 |
| $Tb_2O_3$ | 0.001 to 2.0 |
| $Eu_2O_3$ | 0.001 to 2.0 |
| $Yb_2O_3$ | 0.001 to 2.0 |
| $Gd_2O_3$ | 0.001 to 2.0 |
| $Nd_2O_3$ | 0.001 to 2.0 |
| $Pr_2O_3$ | 0.001 to 2.0 |
| $Dy_2O_3$ | 0.001 to 2.0 |
| $Ag_2O$ | 0.01 to 2.0 |
| $SnO_2$ | 0.01 to 3.0 |
| $Ta_2O_5$ | 0.001 to 2.0. |

12. A process according to claim 10, wherein the additional components are $B_2O_3$, $Na_2O$, BaO, F and/or SrO.

13. A shaped glass ceramic product produced by the process according to claim 1.

14. A glass ceramic product according to claim 13, which has an acid resistance of less than 100 $\mu g/cm^2$.

15. A glass ceramic product according to claim 13, which has a CR value of 0.05 to 0.9, measured at a sample thickness of 1.2 mm.

16. A shaped dental restoration, which contains the glass ceramic product according to claim 13.

17. A shaped dental restoration, according to claim 16, which is an inlay, an onlay, a bridge, an abutment, a facing, a veneer, a facet, a crown or a partial crown.

18. A process according to claim 3, wherein the heat treatment in stage (c) is carried out at a temperature of less than 1000° C.

19. A process according to claim 3, wherein the shaped glass ceramic product of the desired geometry is provided with a coating.

20. A process according to claim 19, wherein the coating is a ceramic, a sintered ceramic, a glass ceramic, a glass, a glaze and/or a composite.

* * * * *